United States Patent
Berthon-Jones et al.

(10) Patent No.: US 6,840,240 B1
(45) Date of Patent: Jan. 11, 2005

(54) CONTROL OF SUPPLIED PRESSURE IN ASSISTED VENTILATION

(75) Inventors: Michael Berthon-Jones, Leonay (AU); Peter John D. Wickham, deceased, late of Five Dock (AU); by Nicola Frances Wickham, legal representative, Five Dock (AU)

(73) Assignee: ResMed Limited, North Ryde (AU)

( * ) Notice: Subject to any disclaimer, the term of this patent is extended or adjusted under 35 U.S.C. 154(b) by 0 days.

(21) Appl. No.: 09/936,854

(22) PCT Filed: May 5, 2000

(86) PCT No.: PCT/AU00/00411

§ 371 (c)(1),
(2), (4) Date: Jan. 2, 2002

(87) PCT Pub. No.: WO00/67826

PCT Pub. Date: Nov. 16, 2000

(30) Foreign Application Priority Data

May 6, 1999 (AU) ............................................. PQ0198

(51) Int. Cl.$^7$ .............................................. F16K 31/02
(52) U.S. Cl. .............................. 128/204.21; 128/204.18
(58) Field of Search ...................... 128/200.24, 203.12, 128/203.14, 203.24, 204.18, 204.21, 204.22, 204.23, 204.26, 204.29, 205.11, 205.14, 205.23, 205.24, 207.14–207.18

(56) References Cited

U.S. PATENT DOCUMENTS

| | | | | |
|---|---|---|---|---|
| 4,466,433 A | * | 8/1984 | Robbins ................ | 128/202.22 |
| 4,550,726 A | * | 11/1985 | McEwen ................ | 128/202.22 |
| 4,957,107 A | * | 9/1990 | Sipin ...................... | 128/204.21 |
| 5,582,182 A | * | 12/1996 | Hillsman ................ | 600/529 |
| 5,596,984 A | * | 1/1997 | O'Mahony et al. ..... | 128/205.24 |
| 5,692,497 A | * | 12/1997 | Schnitzer et al. ...... | 128/204.21 |
| 5,813,399 A | * | 9/1998 | Isaza et al. ............. | 128/204.21 |
| 5,901,704 A | | 5/1999 | Estes et al. ............. | 128/204.23 |
| 6,123,074 A | * | 9/2000 | Hete et al. .............. | 128/205.11 |
| 6,138,675 A | * | 10/2000 | Berthon-Jones ........ | 128/204.23 |

FOREIGN PATENT DOCUMENTS

| | | |
|---|---|---|
| EP | 0 425 092 A1 | 5/1991 |
| WO | WO 97/14462 | 4/1997 |

* cited by examiner

Primary Examiner—Glenn K. Dawson
(74) Attorney, Agent, or Firm—Gottlieb, Rackman & Reisman

(57) ABSTRACT

Methods and apparatus for detecting the occurrence of a potential or actual overpressure during assisted ventilation are described. A blower (10) supplies pressurized gas to a conduit (12), and in turn to a patient mask (11) for connection with the entrance of a patient's airways. A pressure sensor (17, 18) detects the delivered pressure in the mask (11), which is provided to a controller (16). The controller (16) has operation over the blower (10) by way of a servo (19) and motor (20). The controller (16) determines a relatively longterm average of the pressure signal, and compares it against a threshold value (40). If the threshold value is approached or exceeded, the controller (16) controls the blower (10) and thus the supplied pressure to the patient. The effect of the control can be to limit or reduce the supplied gas pressure. The relatively longterm average can be of the order of minutes, or taken over ten or more breaths.

19 Claims, 3 Drawing Sheets

CONTROL OF SUPPLIED PRESSURE IN ASSISTED VENTILATION

FIELD OF THE INVENTION

This invention relates to Non Invasive Positive Pressure Ventilation (NIPPV) treatment apparatus for the provision of assisted ventilation. Particularly, the invention concerns the control of treatment pressure supplied to a subject.

BACKGROUND ART

NIPPV apparatus function to supply a patient with a supply of clean breathable gas (usually air, with or without supplemental oxygen) at a therapeutic pressure or pressures, at appropriate times during the subject's breathing cycle. The therapeutic pressure is also known as the ventilation pressure.

NIPPV apparatus typically include a flow generator, an air filter, a mask, an air delivery conduit connecting the flow generator to the mask, various sensors and a microprocessor-based controller. The flow generator may include a servo-controlled motor and an impeller. The flow generator may also include a valve capable of discharging air to atmosphere as a means for altering the pressure delivered to the patient as an alternative to motor speed control. The sensors measure, amongst other things, motor speed, gas volumetric flowrate and outlet pressure. The apparatus may optionally include a humidifier in the air delivery circuit. The controller may include data storage capacity with or without integrated data retrieval and display functions.

In this specification, NIPPV apparatus will be referred to as "assisted ventilation devices" which, in the broadest form, need not include all of the component features mentioned above.

Assisted ventilation devices are used for the treatment of many conditions, for example respiratory insufficiency or failure due to lung, neuromuscular or musculoskeletal disease and diseases of respiratory control.

Common to all forms of assisted ventilation is the need to control the pressure being applied to the patient. It is a known prior art technique to detect the peak pressure and compare it against a maximum threshold value. If the threshold value is exceeded an alarm state occurs, and corrective action may be taken. This corrective action can be a short-term reduction in supplied pressure, followed by an increase back to the previous pressure.

DISCLOSURE OF THE INVENTION

The present invention is directed to providing an alternative, advantageous approach to the problem of overpressure.

The invention discloses a method for controlling operation of an assisted ventilation device supplying pressurised gas to a patient, the method comprising the steps of:

determining a relatively longterm average of pressure of gas supplied to said patient; and controlling the pressure supplied by said ventilation device with regard to said longterm average.

The invention further discloses a method for detecting the occurrence of a potential or actual overpressure during assisted ventilation, comprising the steps of determining a relatively longterm average of ventilation pressure, and determining whether the average approaches or exceeds a threshold value as being indicative of a potential or actual overpressure occurring.

The invention further discloses a method for controlling operation of an assisted ventilation device supplying pressurised gas to a patient, the method comprising the steps of:

measuring the currently delivered pressure;

determining a relatively longtermn average of the measured pressure; comparing said average against a threshold value; and if the threshold value is approached or exceeded, controlling the pressure supplied by the device.

The invention yet further discloses assisted ventilation apparatus for detecting a potential or actual overpressure condition, comprising:

a blower to supply pressurised gas to a conduct, and in turn to a patient mask for connection with the entrance to a patient's airways:

a pressure sensor to detect the delivered pressure of gas in the conduit or at the mask, and provide a signal thereof; and a controller receiving said pressure signal and having control over operation of the blower and operable to determine a relatively longterm average of the pressure signal and to control the supplied pressure with regard to said longterm average.

The invention yet further discloses assisted ventilation apparatus for detecting a potential or actual overpressure condition, comprising:

a blower to supply pressurised gas to a conduit, and in turn to a patient mask for connection with the entrance to a patient's airways;

a pressure sensor to detect the delivered pressure of gas in the conduit or at the mask, and provide a signal thereof; and a controller, receiving the pressure signal and having control over operation of the blower, and operable to determine a relatively longterm average of the pressure signal. compare the average against a threshold value, and if the threshold value is approached or exceeded, to control the blower and thus the supplied pressure.

In one preferred form, an alarm state exists when said threshold is approached or exceeded, and on the occurrence of an alarm state, the assisted ventilation apparatus issues an alarm. Additionally or alternatively, the blower can be controlled to be switched-off or to be placed in a low pressure standby mode (for example 4 $cmH_2O$).

The invention further discloses a method for controlling operation of an assisted ventilation device supplying pressurised gas to a patient, the method comprising the steps of:

determining a relatively, longtermn average of supplied pressure; and controlling said supplied pressure as a function of a waveform template, a target patient ventilation and said longterm average.

In relation to control of supplied pressure, the blower can be controlled to limit or reduce the supplied pressure. The reduction can be a non-linear function of time and/or pressure. Particularly, the degree of control can be stronger/greater as the threshold value is approached.

The longterm average can, in one form, be of the order of minutes. Alternatively, the average can be over ten or more breaths.

The threshold can be required to be exceeded for a minimum period of time before the alarm state is assessed as occurring.

The invention is advantageous in that it approaches the problem of overpressure from a relatively longer time scale than in the prior art. This is considered to be a more appropriate approach to the medical conditions that attend overpressure in assisted ventilation. For example, sustained overpressure causes a decrease in cardiac output, which would go largely untreated by the prior art arrangement discussed above.

DESCRIPTION OF PREFERRED EMBODIMENTS AND BEST MODE

Figure 1:
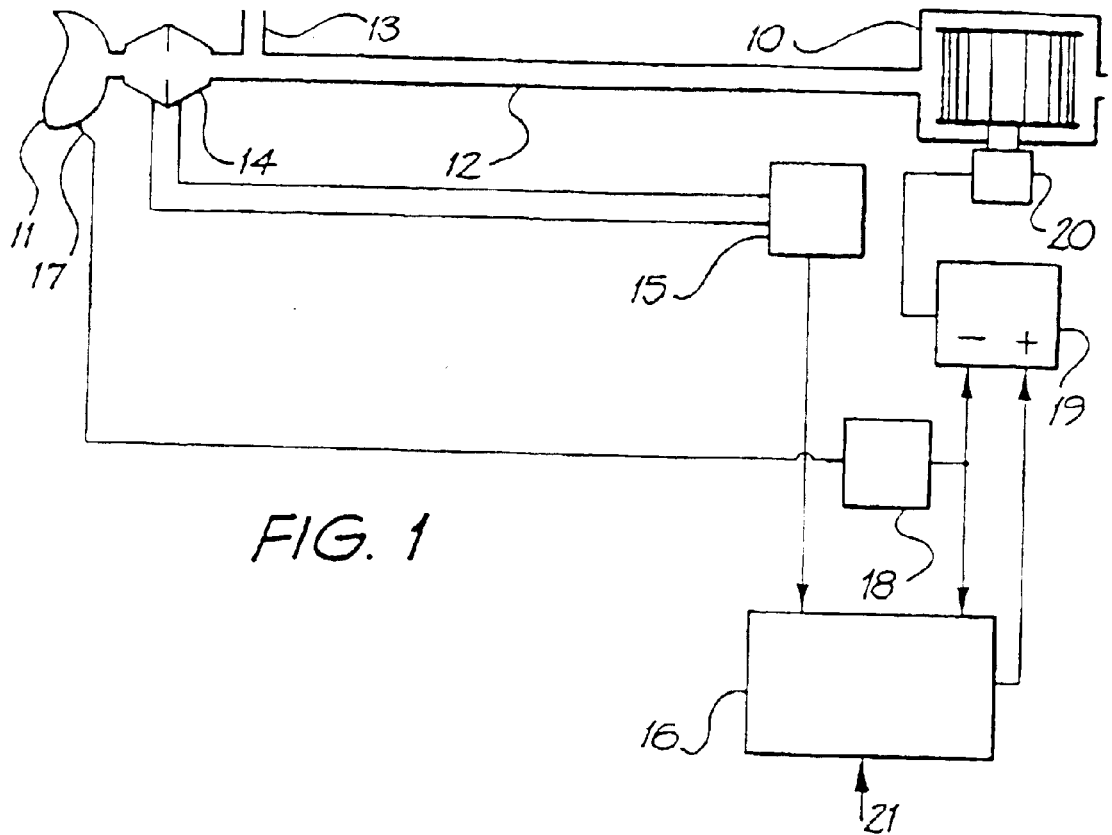
FIG. 1 is a schematic block diagram of a representative assisted ventilation device, in the form of NIPPV apparatus.

An assisted ventilation device embodying one form of the invention is shown in FIG. 1, in which a blower comprising a motor 20 and an impeller 10, supplies breathable gas to a mask 11 for communication with a subject's airway via a delivery tube 12 and exhausting to atmosphere via an exhaust 13. Airflow at the mask 11 is measured using a pneumotachograph 14 and a differential pressure transducer 15. The mask flow signal from the transducer 15 is sampled by a microprocessor 16. Mask pressure is measured at a port 17 using a pressure transducer 18. The pressure signal from the transduces, 15 is also sampled by the microprocessor 16. The microprocessor 16 sends an instantaneous mask pressure request signal to a servo 19, which compares the pressure request signal with the actual pressure signal from the transducer 18 to control a motor 20 driving the impeller 10. The microprocessor's settings can be adjusted via a serial port 21.

It is to be understood that the mask could equally be replaced with a tracheotomy rube, endotracheal tube, nasal pillows, or other means of making a sealed connection between the air delivery means and the subject's airway.

In general terms, the invention is concerned with determining a relatively longterm average of ventilation pressure and avoiding occurrence of overpressure with regard thereto.

In one embodiment, the microprocessor 16 determines the long-term average of the actual treatment pressure, $\overline{p}$, and compares this against a threshold or maximum value, $\overline{P}_{max}$. If the threshold value is exceeded then corrective action may be taken.

The corrective action can be to issue an alarm, to switch-off the assisted ventilation device, to reduce the treatment pressure, or to control the blower in a more complex manner, an example of which is described in more detail below.

Figure 2:
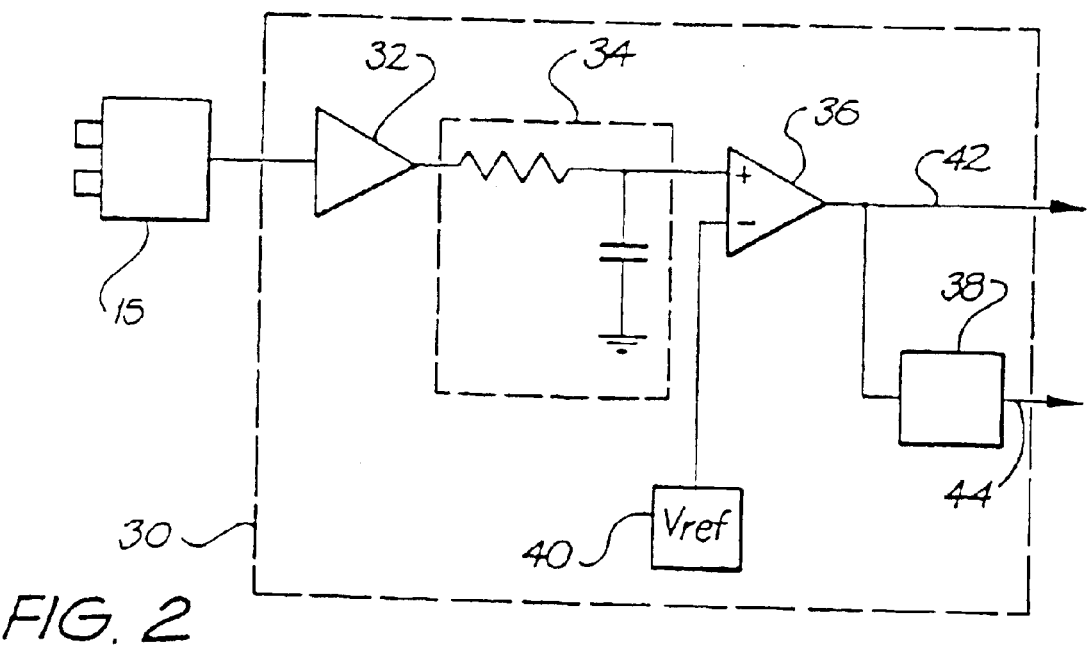
FIG. 2 is a schematic block diagram of an overpressure detection circuit.

As shown in FIG. 2, the circuitry 30 receives a signal from the pressure transducer 15 indicative of the pressure in the air delivery conduit 12. The signal is amplified by an operational amplifier 32, then low-pass filtered 34 with a time constant of approximately one minute. Longer or shorter time constants would be appropriate depending on how long it was considered safe for the subject to be exposed to a relatively high mean pressure. In one embodiment, the time constant can be varied by way of an operator accessible control. The low-pass filtered signal passes to a comparator 36 where it is compared with a reference pressure signal corresponding to 15 cmH$_2$O, representing $\overline{P}_{max}$. The output from the comparator passes to both the servo 19 and a resettable monostable/one-shot 38. The resettable monostable/one-shot 38 is set to 30 seconds. Longer or short time periods would be suitable for specific assisted ventilation applications.

If the output from the comparator 36 is 'true', an indication that the low-pass filter signal exceeds $\overline{P}_{max}$, "reduce" pressure signal is sent to the servo 19 (shown in FIG. 1) on line 42. At this point, the resettable monostable/one-shot 38 starts, to count down. If the count down reaches zero, then a stop signal is sent to the servo 19 on line 44. The count determines an adjustable tolerance on how long the alarm state has occurred before corrective action is taken. If the output from the comparator 36 is "false", there is no alarm state, and the resettable monostable/one-shot 38 is reset.

In another embodiment, implemented in software, the avoidance of overpressure is approached as the continuous monitoring of pressure as a function of the longterm average of the pressure. Referring once again to FIG. 1, the microprocessor 16 receives a signal representing mask pressure from the transducer 18. The microprocessor 16 controls the servo 19 such that the desired treatment pressure achieved satisfies the following equation:

$$P = P_0 + k.A.f(v,t) \quad [1]$$

where:

P is the pressure setting for the blower (degree of support) (cmH$_2$O);

P$_0$ is a constant, the baseline pressure, chosen, for example, to keep the upper airway open, or to balance intrinsic PEEP (cmH$_2$O).

In one form, $$k=1 \quad [2a]$$

In other forms, $$k=k', \text{ low pass filtered with time constant of 5 seconds} \quad [2b]$$

where:

$$k' = \begin{cases} 0, & \overline{p} \geq 15 \text{ cm H}_2\text{O} \\ 0.1, & \overline{p} = 14.9 \text{ cm H}_2\text{O} \\ 1, & \overline{p} \leq 14.5 \text{ cm H}_2\text{O} \end{cases} \quad [3]$$

and linearly in between.

The purpose of making k nonlinear on $\overline{p}$ is to provide strong control as $\overline{P}_{max}$ is approached, with less effect further away from $\overline{P}_{max}$. The purpose of low pass filtering is to reduce distortion of the within-breath pressure-time profile.

The pressure modulation amplitude, A (cm H$_2$O) is given by:

$$A = g\int(V_e - V_{TGT})dt \quad [4]$$

where g is a constant, ie is the minute ventilation, and V$_{TGT}$ is the target ventilation. A may be truncated to lie between A$_{max}$ and A$_{min}$.

f is a function of at least one of time, t, and respiratory airflow, v, chosen to produce the desired pressure waveform. A range of functions is known to those skilled in the art. One example function corresponding to a spontaneous mode bi-level ventilator is:

$$f(v,t) = \begin{cases} 1, & v > 0 \\ 0 & \text{otherwise} \end{cases} \quad [5a]$$

Another example function is:

$$f(v,t) = \begin{cases} 1, & t' < T_i \\ 0, & \text{otherwise} \end{cases} \quad [5b]$$

where:
t'=t modulo $T_{not}$
$T_i$=duration of inspiration
$T_{not}$=duration of a breath
This corresponds to a "timed-mode" bilevel ventilator, with
P=$P_0$ during expiration; and
P=$P_0$+A during inspiration A number of simulations have been performed to demonstrate an embodiment of the invention in practise.

Figure 3:
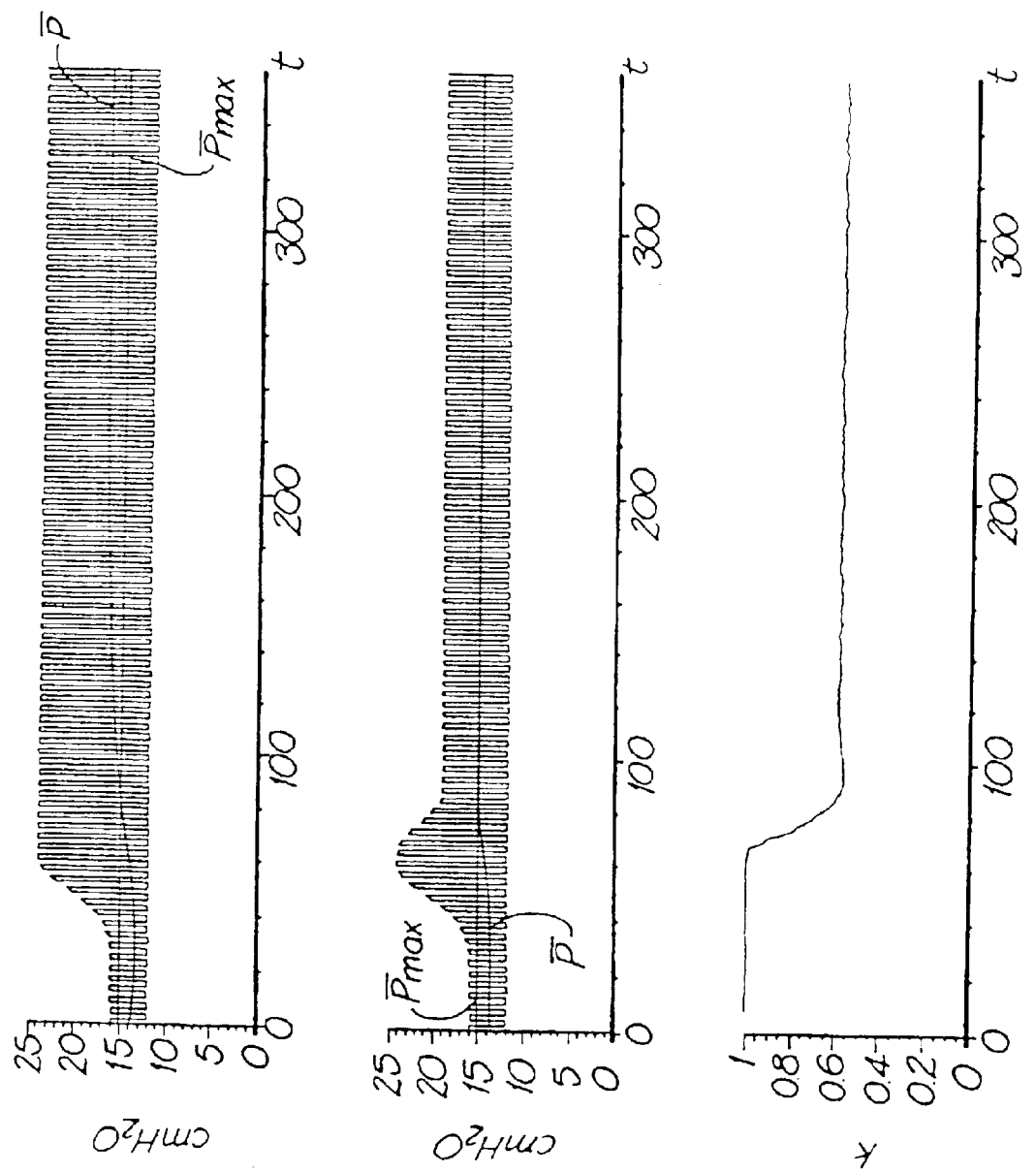
FIG. 3 shows traces of treatment pressure with time and the operation of an embodiment of the invention.

In FIG. 3, there is a sustained rise in peak pressure. In the top trace is shown the effect without the use of the present invention. The mean pressure exceeds a chosen $\bar{P}_{max}$ of 15 cmH$_2$O, which is undesirable. In the second trace, this is corrected by an embodiment of the invention, where the mean pressure is kept close to $\bar{P}_{max}$. The bottom trace shows the factor "k", and how it decreases from unity to approximately 0.5.

Figure 4:
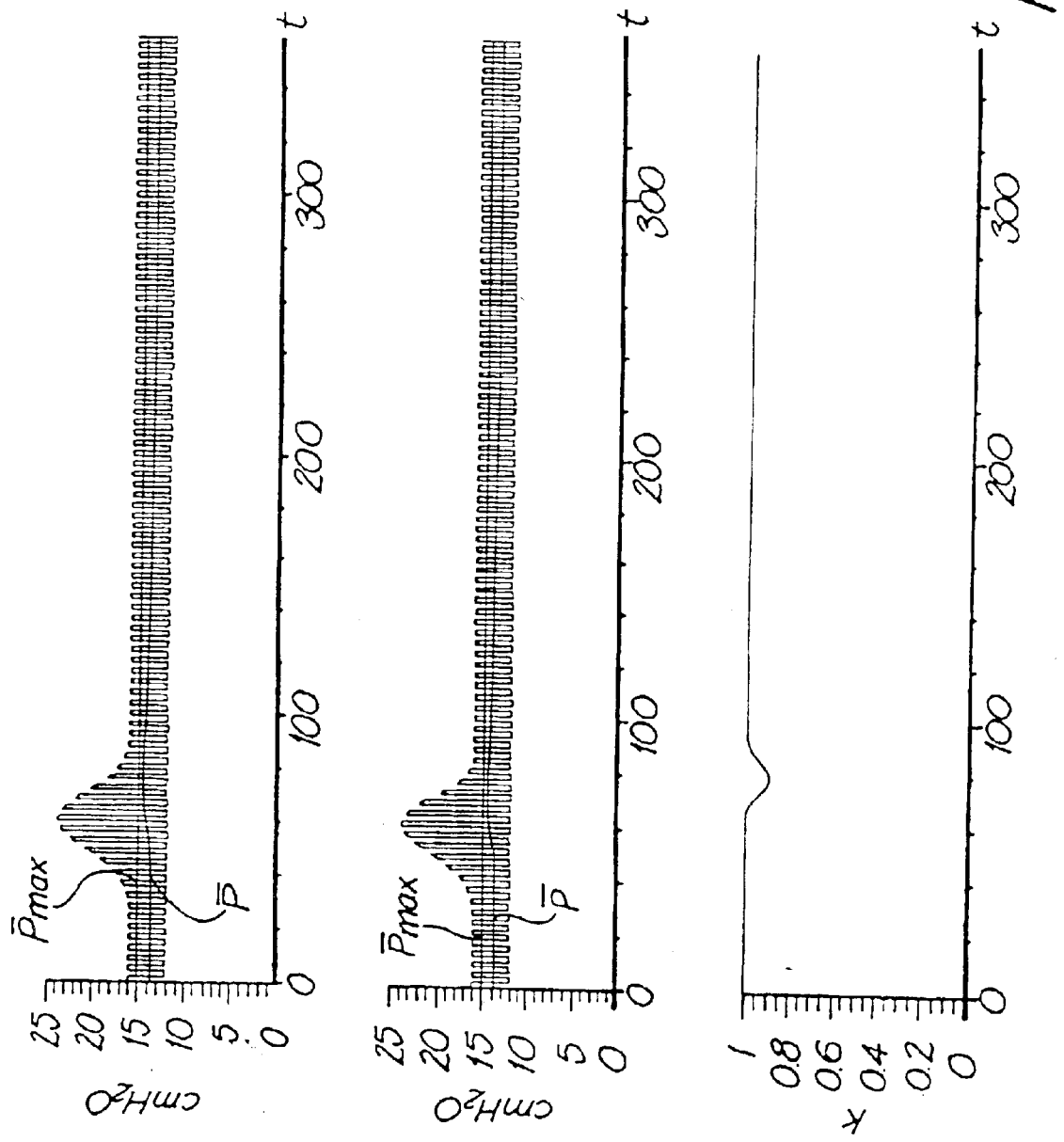
FIG. 4 shows further traces of treatment pressure with time and the operation of an embodiment of the invention.

In FIG. 4, there is a transient rise in peak pressure. In the top trace, even without the practise of invention, the mean pressure closely approaches but does not exceed $\bar{P}_{max}$, which is permissible, even though the instantaneous pressure goes very high. With the invention practised, (second trace), the resultant pressure is little affected, because k remains close to unity (bottom trace)

In this embodiment, as the mean pressure threshold is approached, the degree of assistance is gradually reduced or limited. In another embodiment, both the baseline pressure, $P_0$, and amplitude of ventilatory support, A, are progressively reduced as the mean pressure, $\bar{P}$, approaches the desired threshold pressure, $\bar{P}_{max}$.

The invention has been described with reference to a number of non-limiting examples, and it will be appreciated that the invention can be embodied in numerous other forms.

What is claimed is:

1. A method for controlling operation of an assisted ventilation device supplying pressurized gas to a patient, the method comprising the steps of:
   determining an average of pressure of gas supplied to said patient; and
   controlling the pressure supplied by said ventilation device with regard to said average,
   wherein, said controlling step includes a condition that the average exceeds a threshold for more than a minimum period of time before a potential or actual overpressure is determined as occurring.

2. A method as claimed in claim 1, comprising the further step of issuing an alarm upon the determination of a potential or actual overpressure occurring.

3. A method as claimed in claim 2, wherein said controlling step includes limiting or reducing supplied gas pressure to the patient.

4. A method as claimed in claim 3, wherein, for the case of reducing supplied gas pressure, the reducing step is a non-linear function of time and/or pressure.

5. A method as claimed in claim 4, wherein the degree of reduction is greater as said threshold value is approached.

6. A method for controlling operation of an assisted ventilation device supplying pressurized gas to a patient, the method comprising the steps of:
   measuring the currently delivered pressure;
   determining an average of the measured pressure;
   comparing said average against a threshold value; and
   if the threshold value is approached or exceeded, controlling the pressure supplied by the device,
   wherein, for the case of said average exceeding said threshold, said controlling step includes a condition that said excess must occur for a minimum period of time before it is determined that a potential or actual overpressure is occurring.

7. A method as claimed in one of claims 6,3,4, and 5, wherein said average is of the order of minutes.

8. A method as claimed in one of claims 6,3,4, and 5, wherein said average is taken over ten or more breaths.

9. A method for controlling operation of an assisted ventilation device supplying pressurized gas to a patient, the method comprising the steps of:
   determining an average of supplied pressure; and
   controlling said supplied pressure as a function of a waveform template, a target patient ventilation and said average, wherein said function is given by:

$$P = P_0 + k.A.f(v,t)$$

where:
P is said supplied pressure,
$P_0$ is a constant pressure,
K is a function of said average,
A is a function of said target patient ventilation, and f(v,t) represents said waveform template.

10. A method as claimed in claim 9 wherein, in said controlling step, when said average approaches a threshold value, strong control of said supplied pressure is provided.

11. Assisted ventilation apparatus for detecting a potential or actual overpressure condition, comprising:
   a blower to supply pressurized gas to a conduit, and in turn to a patient mask for connection with the entrance to a patient's airways:
   a pressure sensor to detect the delivered pressure of gas in the conduit or at the mask, and provide a signal thereof; and
   a controller receiving said pressure signal and having control over operation of the blower and configured to determine an average of the pressure signal and to control the supplied pressure with regard to said average,
   wherein, said control of the supplied pressure includes a condition that the average exceeds a threshold for more than a minimum period of time before a potential or actual overpressure is determined as occurring.

12. Assisted ventilation apparatus as claimed in claim 11, wherein said controller controls the supplied pressure as a function of a waveform template, a target patient ventilation and said average.

13. Assisted ventilation apparatus for detecting a potential or actual overpressure condition, comprising:
   a blower to supply pressurized gas to a conduit, and in turn to a patient mask for connection with the entrance to a patient's airways;
   a pressure sensor to detect the delivered pressure of gas in the conduit or at the mask, and provide a signal thereof; and a controller, receiving the pressure signal and having control over operation of the blower, and configured to determine an average of the pressure signal, compare the average against a threshold value, and if the threshold value is approached or exceeded, to control the blower and thus the supplied pressure, wherein, the controller is further configured for determining a time that the average exceeds the threshold and conditioning the control of the blower on the time exceeding a minimum period.

14. Apparatus as claimed in claim 13, wherein said controller controls the supplied pressure by limitation or reduction.

15. Apparatus as claimed in claim 14, wherein, for the case of reducing supplied pressure, the controller reduces the pressure as a non-linear function of time and/or pressure.

16. Apparatus as claimed in claim 15, wherein the degree of reduction by the controller is greater as said threshold value is approached.

17. Apparatus as claimed in one of claims 13–16, further comprising alarm signaling means, coupled to said controller, for indicating that an alarm state exists if the threshold value is approached or exceeded.

18. Apparatus as claimed in one of claims 13–16, wherein said controller determines the average in the order of minutes.

19. Apparatus as claimed in one of claims 13–16, wherein said controller determines the average over ten or more breaths.

* * * * *